(12) United States Patent
Carter

(10) Patent No.: US 11,505,397 B1
(45) Date of Patent: Nov. 22, 2022

(54) STERILE GLOVE DISPENSING ASSEMBLY

(71) Applicant: William Carter, Spring Lake, TN (US)

(72) Inventor: William Carter, Spring Lake, TN (US)

( * ) Notice: Subject to any disclaimer, the term of this patent is extended or adjusted under 35 U.S.C. 154(b) by 0 days.

(21) Appl. No.: 17/399,525

(22) Filed: Aug. 11, 2021

(51) Int. Cl.
*B65D 83/08* (2006.01)
*A61B 42/40* (2016.01)
*B65D 25/22* (2006.01)

(52) U.S. Cl.
CPC .......... *B65D 83/0894* (2013.01); *A61B 42/40* (2016.02); *B65D 25/22* (2013.01); *B65D 83/0805* (2013.01); *B65D 2583/082* (2013.01)

(58) Field of Classification Search
CPC .................................................. B65D 83/0894
See application file for complete search history.

(56) References Cited

U.S. PATENT DOCUMENTS

| | | | |
|---|---|---|---|
| 4,997,105 A | 3/1991 | Fischer | |
| 5,816,440 A | 10/1998 | Shields | |
| 6,021,919 A * | 2/2000 | Kelly | A61B 42/40 221/281 |
| 6,543,642 B1 | 4/2003 | Milliorn | |
| 8,960,493 B1 | 2/2015 | Dennison | |
| 2005/0066413 A1 | 3/2005 | Mattesky | |
| 2007/0215630 A1 * | 9/2007 | Tramontina | A61B 42/40 221/46 |
| 2008/0314920 A1 * | 12/2008 | Rodrigues | A61B 50/20 221/63 |
| 2014/0061220 A1 * | 3/2014 | Kowal | B65D 83/0805 221/135 |
| 2016/0051330 A1 * | 2/2016 | Cosentino, II | A61B 42/40 221/45 |
| 2016/0152403 A1 * | 6/2016 | Ray | B65D 83/0811 221/33 |

* cited by examiner

*Primary Examiner* — Gene o Crawford
*Assistant Examiner* — Ayodeji T Ojofeitimi

(57) ABSTRACT

A sterile glove dispensing assembly includes a container for storing a plurality of sterile gloves. The container has a dispensing opening and the plurality of sterile gloves is strategically oriented that a cuff of each of the sterile gloves extends outwardly through the dispensing opening. In this way a user can draw the sterile gloves outwardly from the container without touching fingers of the sterile gloves for retaining sterility of the fingers. A box is included for insertably receiving the container and a dispensing slot is integrated into the box. The dispensing opening in the container is aligned with the dispensing slot when the container is positioned inside of the box thereby facilitating the sterile gloves to be drawn outwardly from the dispensing slot.

8 Claims, 6 Drawing Sheets

STERILE GLOVE DISPENSING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to glove dispensing device and more particularly pertains to a new glove dispensing device for preserving sterility of sterile gloves when the sterile gloves are drawn from a dispenser. The device includes a container that has a dispensing chute and a plurality of sterile gloves that are strategically positioned in the container such that a cuff of the sterile gloves extends outwardly from the dispensing chute. Additionally, a box is provided into which the container can be positioned. A plurality of couplers is attached to the box for retaining the box at a selected location.

(2) Description of Related Art Including Information Disclosed Under 37 CFR 1.97 and 1.98

The prior art relates to glove dispensing devices including a glove dispenser that includes a container in which a plurality of sterile gloves are stored and which are oriented such that a cuff of the sterile gloves extends outwardly from the container. The prior art discloses a sterile glove dispenser that includes a box and a pouch which contains a plurality of sterile gloves and which can be positioned in the box. The prior art discloses a glove dispensing system that includes a plurality of sterile gloves, each being oriented in an upside down position thereby facilitating a user to insert their hand into the sterile gloves without touching an outside of the sterile gloves. The prior art discloses a glove dispensing container that contains a plurality of connected pairs of gloves, each strategically positioned to protect fingers of the gloves from being touched when the gloves are donned.

BRIEF SUMMARY OF THE INVENTION

An embodiment of the disclosure meets the needs presented above by generally comprising a container for storing a plurality of sterile gloves. The container has a dispensing opening and the plurality of sterile gloves is strategically oriented that a cuff of each of the sterile gloves extends outwardly through the dispensing opening. In this way a user can draw the sterile gloves outwardly from the container without touching fingers of the sterile gloves for retaining sterility of the fingers. A box is included for insertably receiving the container and a dispensing slot is integrated into the box. The dispensing opening in the container is aligned with the dispensing slot when the container is positioned inside of the box thereby facilitating the sterile gloves to be drawn outwardly from the dispensing slot.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
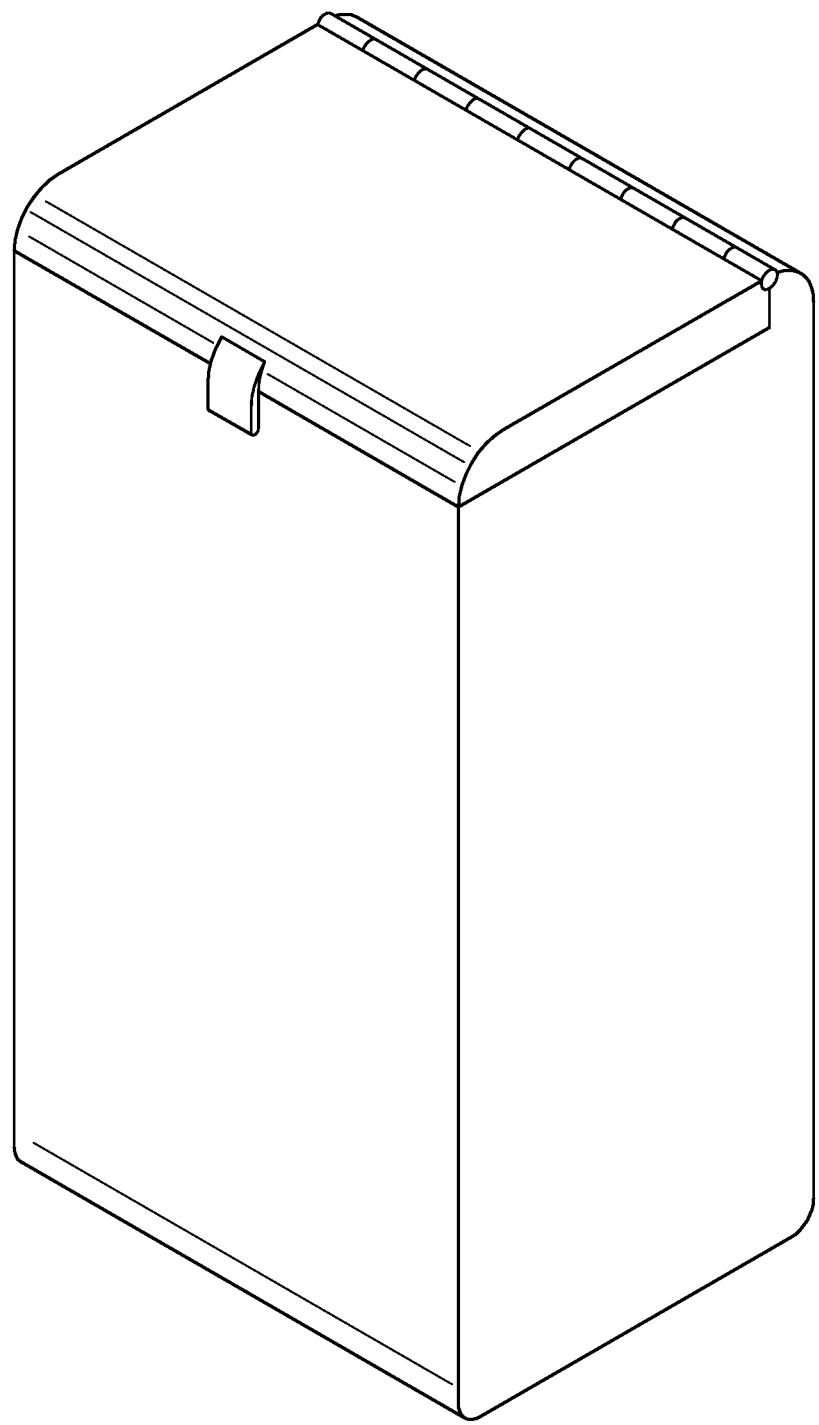
FIG. 1 is a front perspective view of a sterile glove dispensing assembly according to an embodiment of the disclosure.
Figure 2:
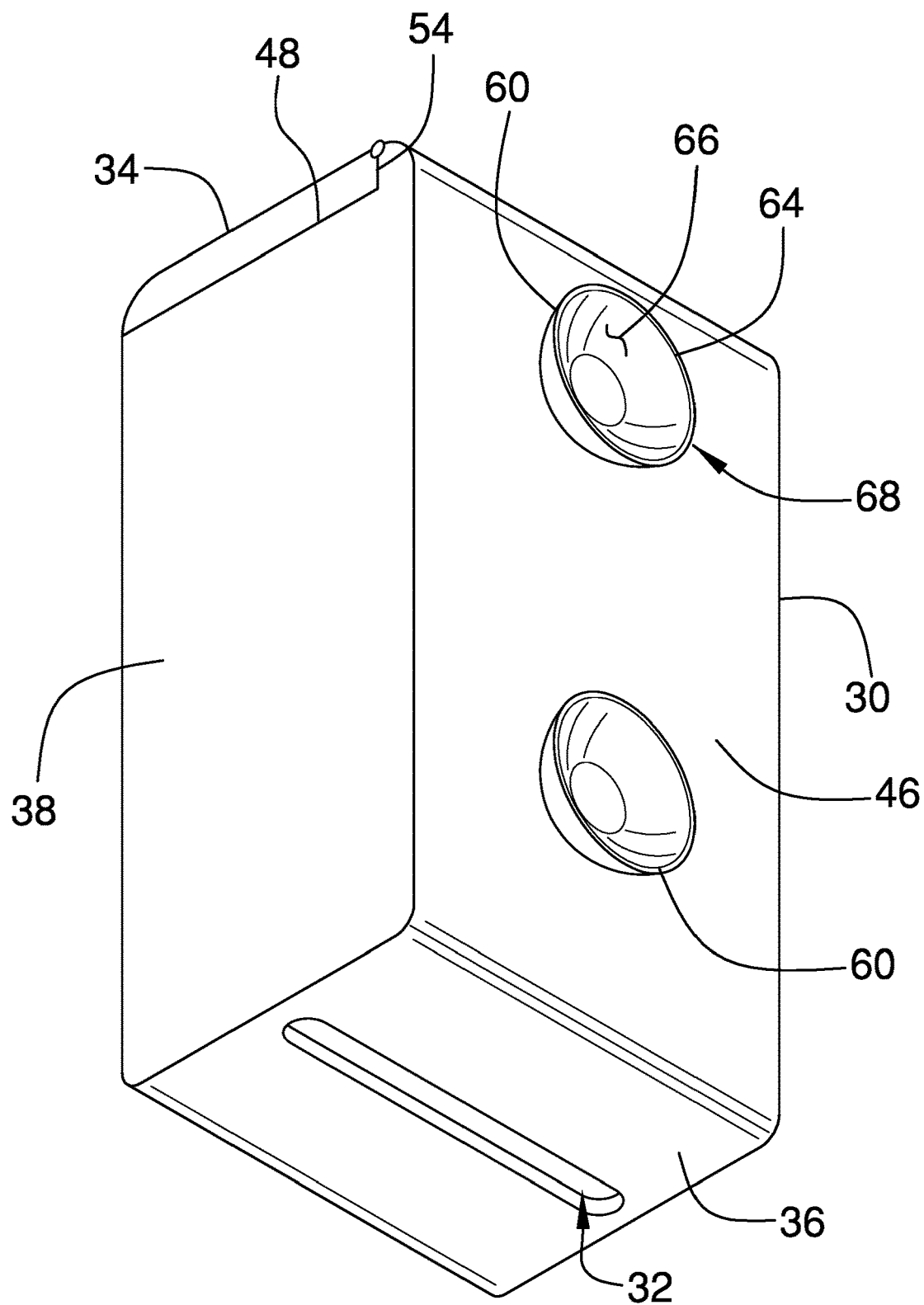
FIG. 2 is a back perspective view of an embodiment of the disclosure.
Figure 3:
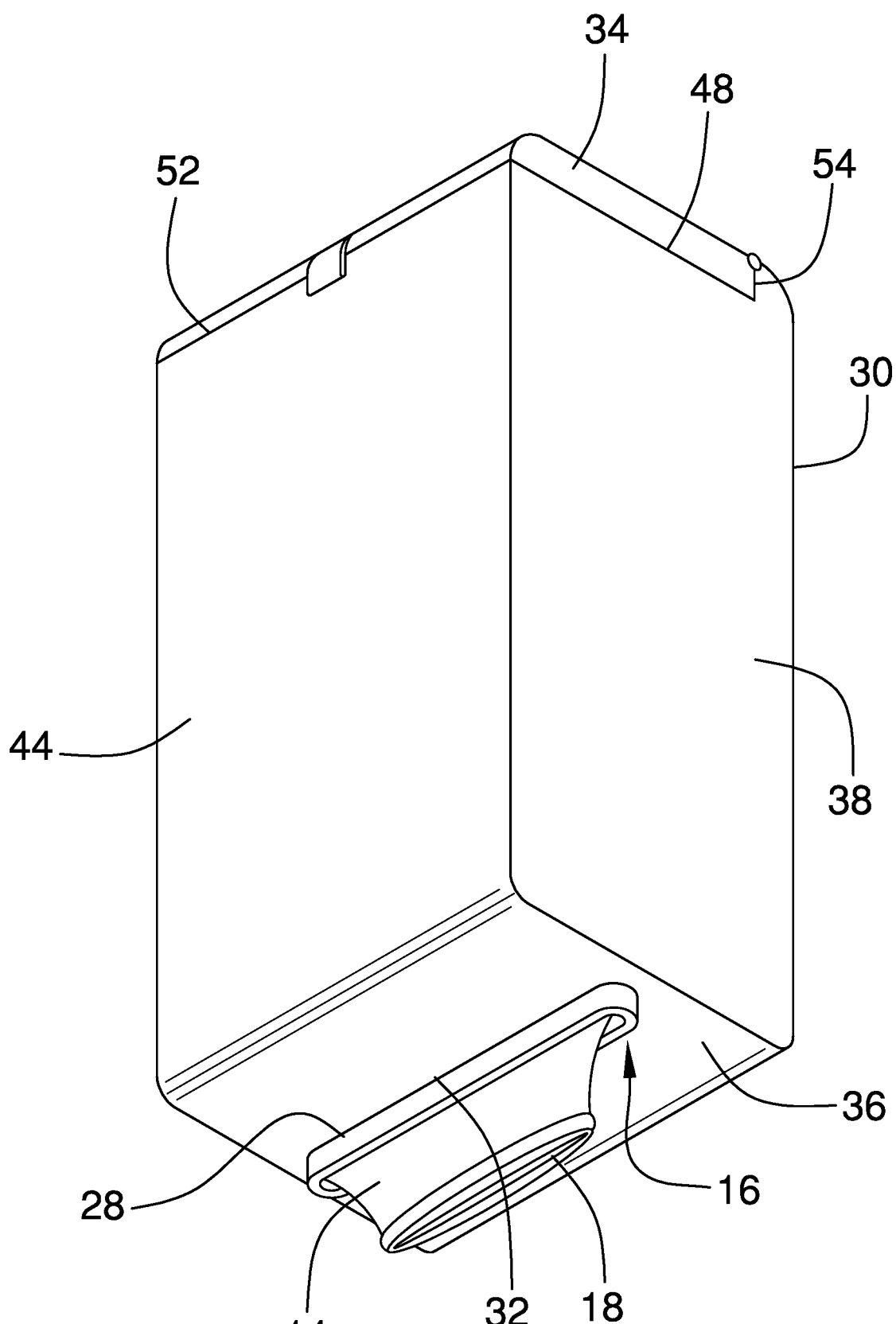
FIG. 3 is a bottom perspective view of an embodiment of the disclosure.
Figure 4:
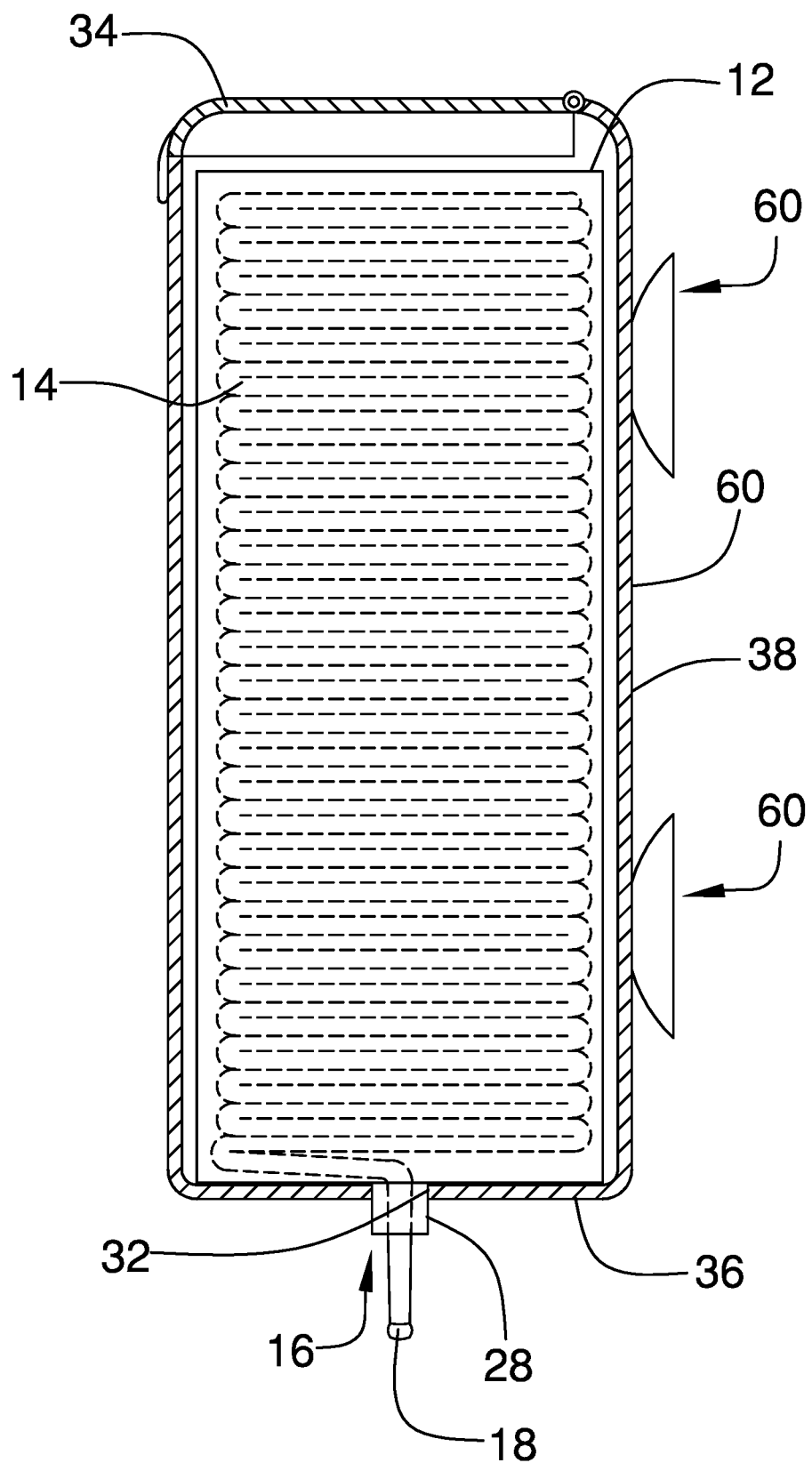
FIG. 4 is a cross sectional view taken along line 4-4 of FIG. 1 of an embodiment of the disclosure.
Figure 5:
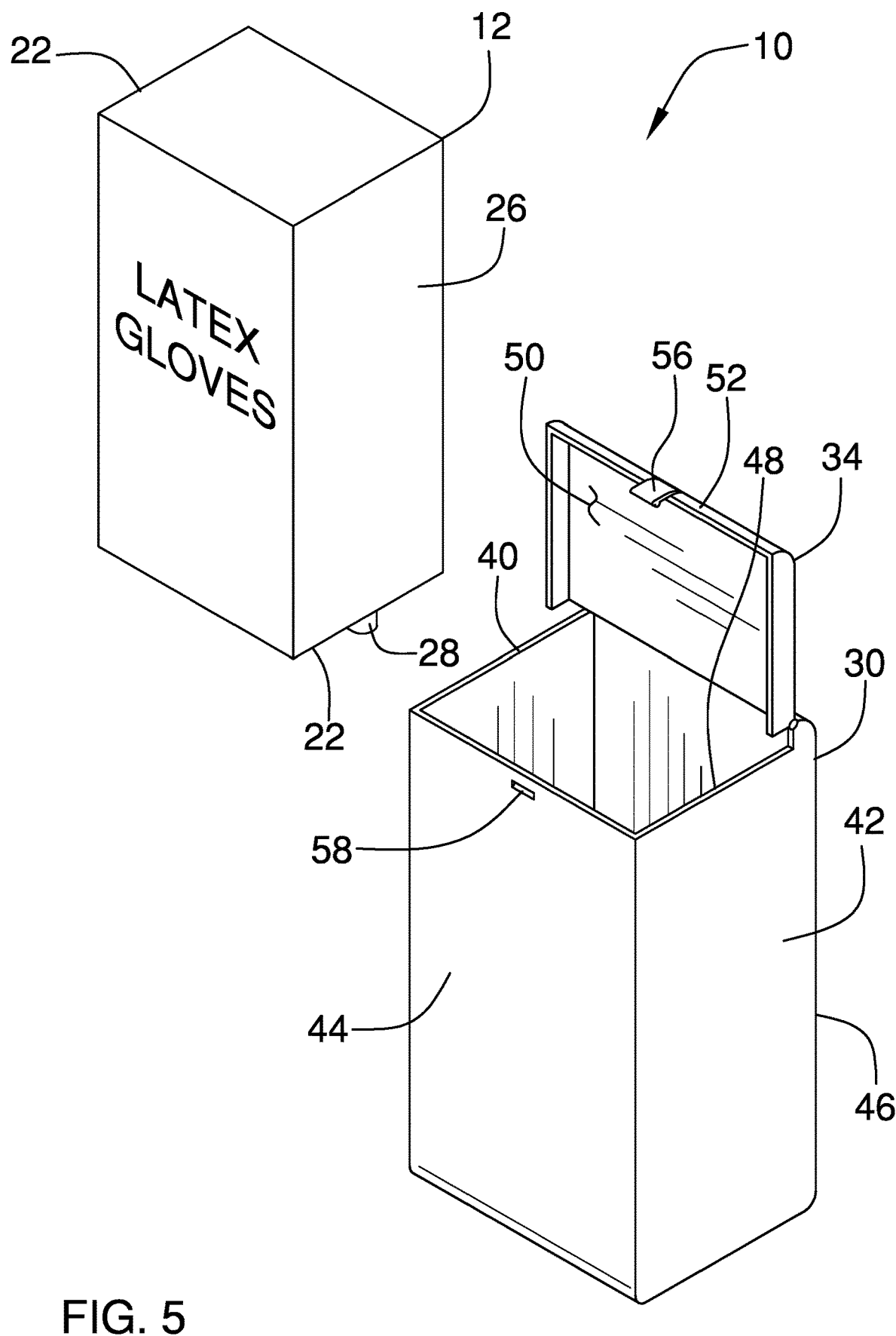
FIG. 5 is an exploded perspective view of an embodiment of the disclosure.
Figure 6:
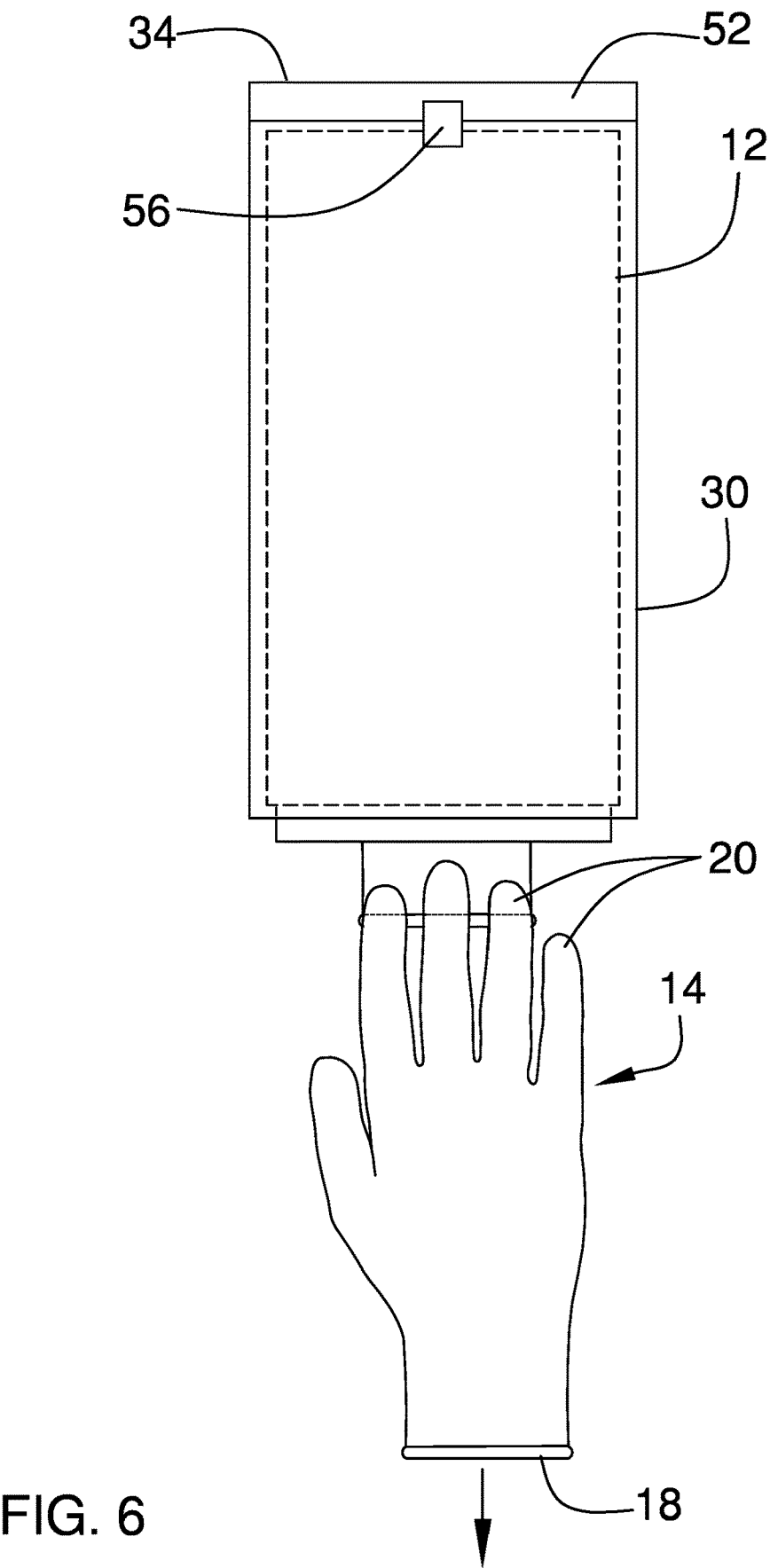
FIG. 6 is a perspective in-use view of an embodiment of the disclosure.

With reference now to the drawings, and in particular to FIGS. 1 through 6 thereof, a new glove dispensing device embodying the principles and concepts of an embodiment of the disclosure and generally designated by the reference numeral 10 will be described.

As best illustrated in FIGS. 1 through 6, the sterile glove dispensing assembly 10 generally comprises a container 12 for storing a plurality of sterile gloves 14 that includes a dispensing opening 16 that is integrated into the container 12. The plurality of sterile gloves 14 is strategically oriented in the container 12 such that a cuff 18 of each of the sterile gloves 14 extends outwardly through the dispensing opening 16. In this way the plurality of sterile gloves 14 facilitates a user to draw the sterile gloves 14 outwardly from the container 12 without touching fingers 20 of the sterile gloves 14 thereby retaining sterility of the fingers 20. Thus, the sterilize gloves 14 can be worn for performing food service work, for example, without the fear of contaminating the fingers 20 of the sterile glove 14 when the sterile glove 14 is being donned.

The container 12 has a bottom wall 22, a first lateral wall 24 and a second lateral wall 26, and the bottom wall 22 has a chute 28 extending downwardly from the bottom wall 22. The chute 28 is open and the chute 28 is in fluid communication with an interior of the container 12 such that the chute 28 defines the dispensing opening 16. Moreover, the chute 28 is elongated to extend substantially between the first lateral wall 24 and the second lateral wall 26. The container 12 may be a cube shaped box that is filled with the sterile gloves 14 during the manufacturing process. Additionally, the sterile gloves 14 may comprise latex gloves, non-latex gloves, rubber gloves or any other type of disposable, sterile gloves.

A box 30 is provided for insertably receiving the container 12 and a dispensing slot 32 is integrated into the box 30. The dispensing opening 16 in the container 12 is aligned with the dispensing slot 32 when the container 12 is positioned inside of the box 30. In this way the sterile gloves 14 can be drawn outwardly from the dispensing slot 32. The box 30 includes a lid 34 that is hingedly integrated onto the box 30 for opening and closing the box 30. The box 30 has a lower wall 36 and a perimeter wall 38 extending upwardly from the lower wall 36, and perimeter wall 38 has a first lateral side 40, a second lateral side 42, a front side 44 and a rear side 46. The dispensing slot 32 extends through the lower wall 36 and the dispensing slot 32 is elongated to extend substantially between the first lateral side 40 and the second lateral side 42.

The chute 28 extends downwardly through the dispensing slot 32 when the container 12 is positioned inside of the box 30. The perimeter wall 38 has a distal edge 48 with respect to the bottom wall 22, and each of the front side 44, the first lateral side 40 and the second lateral side 42 has a height that is less than the height of the rear side 46. Thus, the distal edge 48 corresponding to each of the front side 44, the first lateral side 40 and the second lateral side 42 is recessed with respect to the distal edge 48 corresponding to the rear side 46. The lid 34 has a lower surface 50, a front side 52 and a back side 54, and the back side 54 is hingedly coupled to the distal edge 48 of the perimeter wall 38 corresponding to the rear side 46 of the perimeter wall 38. Furthermore, the lower surface 50 rests on the distal edge 48 corresponding to each of the front side 44, the first lateral side 40 and the second lateral side 42 of the perimeter wall 38 when the lid 34 is closed. The lid 34 extends upwardly from the perimeter wall 38 when the lid 34 is opened.

A latch 56 is coupled to the front side 44 of the lid 34 and the latch 56 engages an engagement point 58 on the front side 44 of the perimeter wall 38 of the housing when the lid 34 is closed. In this way the lid 34 is releasably retained in a closed position. A pair of couplers 60 is each coupled to the box 30 and each of the couplers 60 releasably engages a support surface 62 for retaining the box 30 on the support surface 62. Each of the couplers 60 is positioned on the rear side 46 of the perimeter wall 38 of the box 30 and each of the couplers 60 has a distal end 64 with respect to the rear side 46 and a first surface 66. The first surface 66 of each of the couplers 60 is concavely arcuate between the rear side 46 and the distal end 64 such that each of the couplers 60 forms a suction cup 68 that can be compressed against the support surface 62 for suctionally engaging the support surface 62.

In use, the container 12 is inserted into the box 30 such that the chute 28 extends outwardly through the dispensing slot 32 in the box 30. In this way the cuff 18 of a respective sterile glove 14 is available to be pulled downwardly out of the box 30. Thus, the respective sterile glove 14 can be donned without compromising the sterility of the fingers 20 of the sterile glove 14. In this way the sterile gloves 14 ensure compliance with food safety regulations, for example, or other conditions that require protection against touch transmitted bacteria and viruses. The couplers 60 facilitate the box 30 to be located at a variety of different locations that suit the needs of the users. The container 12 is removed and replaced when the sterile gloves 14 are depleted.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sterile glove dispensing assembly for dispending sterile gloves cuff first to maintain sterility of fingers of the sterile gloves, said assembly comprising:

a container for storing a plurality of sterile gloves, said container having a dispensing opening being integrated into said container, said plurality of sterile gloves being strategically oriented in said container such that a cuff of each of said sterile gloves extends outwardly through said dispensing opening wherein said plurality of sterile gloves is configured to facilitate a user to draw said sterile gloves outwardly from said container without touching fingers of said sterile gloves thereby retaining sterility of said fingers;

a box for insertably receiving said container, said box having a dispensing slot being integrated into said box, said dispensing opening in said container being aligned with said dispensing slot when said container is positioned inside of said box thereby facilitating said sterile gloves to be drawn outwardly from said dispensing slot, said box including a lid being hingedly integrated onto said box for opening and closing said box; and a pair of couplers, each of said couplers being coupled to said box, each of said couplers releasably engaging a support surface for retaining said box on the support surface.

2. The assembly according to claim 1, wherein each of said couplers is positioned on a rear side of a perimeter wall of said box, each of said couplers having a distal end with respect to said rear side and a first surface, said first surface of each of said couplers being concavely arcuate between said rear side and said distal end such that each of said couplers forms a suction cup wherein said suction cup is configured to be compressed against the support surface for suctionally engaging the support surface.

3. The assembly according to claim 1, wherein:
said container has a bottom wall, a first lateral wall and a second lateral wall, said bottom wall having a chute extending downwardly from said bottom wall, said chute being open, said chute being in fluid communication with an interior of said container such that said chute defines said dispensing opening, said chute being elongated to extend substantially between said first lateral wall and said second lateral wall; and
said box has a lower wall and a perimeter wall extending upwardly from said lower wall, perimeter wall having a first lateral side, a second lateral side, a front side and a rear side, said dispending slot extending through said lower wall, said dispensing slot being elongated to extend substantially between said first lateral side and said second lateral side, said chute extending downwardly through said dispensing slot when said container is positioned inside of said box.

4. The assembly according to claim 1, wherein said box has a bottom wall and a perimeter wall extending upwardly from said bottom wall, said perimeter wall having a front side, a rear side, a first lateral side and a second lateral side, said perimeter wall has a distal edge with respect to said bottom wall, each of said front side, said first lateral side and said second lateral side having a height being less than the height of said rear side such that said distal edge corresponding to each of said front side, said first lateral side and said second lateral side is recessed with respect to said distal edge corresponding to said rear side.

5. The assembly according to claim 4, wherein said lid has a lower surface, a front side and a back side, said back side being hingedly coupled to said distal edge of said perimeter wall corresponding to said rear side of said perimeter wall, said lower surface resting on said distal edge corresponding to each of said front side, said first lateral side and said second lateral side of said perimeter wall when said lid is closed, said lid extending upwardly from said perimeter wall when said lid is opened.

6. The assembly according to claim 5, further comprising a latch being coupled to said front side of said lid, said latch engaging an engagement point on said front side of said perimeter wall of said housing when said lid is closed for releasably retaining said lid in a closed position.

7. A sterile glove dispensing assembly for dispensing sterile gloves cuff first to maintain sterility of fingers of the sterile gloves, said assembly comprising:
a container for storing a plurality of sterile gloves, said container having a dispensing opening being integrated into said container, said plurality of sterile gloves being strategically oriented in said container such that a cuff of each of said sterile gloves extends outwardly through said dispensing opening wherein said plurality of sterile gloves is configured to facilitate a user to draw said sterile gloves outwardly from said container without touching fingers of said sterile gloves thereby retaining sterility of said fingers, said container having a bottom wall, a first lateral wall and a second lateral wall, said bottom wall having a chute extending downwardly from said bottom wall, said chute being open, said chute being in fluid communication with an interior of said container such that said chute defines said dispensing opening, said chute being elongated to extend substantially between said first lateral wall and said second lateral wall;

a box for insertably receiving said container, said box having a dispensing slot being integrated into said box, said dispensing opening in said container being aligned with said dispensing slot when said container is positioned inside of said box thereby facilitating said sterile gloves to be drawn outwardly from said dispensing slot, said box including a lid being hingedly integrated onto said box for opening and closing said box, said box having a lower wall and a perimeter wall extending upwardly from said lower wall, perimeter wall having a first lateral side, a second lateral side, a front side and a rear side, said dispending slot extending through said lower wall, said dispensing slot being elongated to extend substantially between said first lateral side and said second lateral side, said chute extending downwardly through said dispensing slot when said container is positioned inside of said box, said perimeter wall having a distal edge with respect to said bottom wall, each of said front side, said first lateral side and said second lateral side having a height being less than the height of said rear side such that said distal edge corresponding to each of said front side, said first lateral side and said second lateral side is recessed with respect to said distal edge corresponding to said rear side, said lid having a lower surface, a front side and a back side, said back side being hingedly coupled to said distal edge of said perimeter wall corresponding to said rear side of said perimeter wall, said lower surface resting on said distal edge corresponding to each of said front side, said first lateral side and said second lateral side of said perimeter wall when said lid is closed, said lid extending upwardly from said perimeter wall when said lid is opened;

a latch being coupled to said front side of said lid, said latch engaging an engagement point on said front side of said perimeter wall of said housing when said lid is closed for releasably retaining said lid in a closed position; and a pair of couplers, each of said couplers being coupled to said box, each of said couplers releasably engaging a support surface for retaining said box on the support surface, each of said couplers being positioned on said rear side of said perimeter wall of said box, each of said couplers having a distal end with respect to said rear side and a first surface, said first surface of each of said couplers being concavely arcuate between said rear side and said distal end such that each of said couplers forms a suction cup wherein said suction cup is configured to be compressed against the support surface for suctionally engaging the support surface.

8. A method is dispensing sterile gloves in a manner the preserves sterility of said sterile glove, the steps of the method comprising:
providing a container having a chute extending downwardly from said container;
providing a plurality of sterile gloves;
packaging said plurality of sterile in a strategic manner to facilitate a cuff of each of said sterile gloves to extend outwardly through said chute in said container;
providing a box having a dispensing opening being integrated into said box;
inserting said container into said box having said chute on said container extending outwardly through said dispensing opening in said box; and
grasping said cuff on said sterile glove that extends outwardly through said chute; and drawing said sterile glove outwardly from said chute thereby facilitating said sterile glove to be worn without touching fingers of said sterile glove for preserving sterility of said fingers.

\* \* \* \* \*